(12) United States Patent
Puckette et al.

(10) Patent No.: US 9,861,970 B2
(45) Date of Patent: Jan. 9, 2018

(54) HYDROFORMYLATION CATALYST

(71) Applicant: Eastman Chemical Company, Kingsport, TN (US)

(72) Inventors: Thomas Allen Puckette, Longview, TX (US); Xiaopeng Shan, Plano, TX (US); Jody Lee Rodgers, Gilmer, TX (US); Brian E. Green, Arp, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/372,934

(22) Filed: Dec. 8, 2016

(65) Prior Publication Data

US 2017/0087542 A1 Mar. 30, 2017

Related U.S. Application Data

(62) Division of application No. 15/180,823, filed on Jun. 13, 2016, now Pat. No. 9,550,179.

(60) Provisional application No. 62/216,038, filed on Sep. 9, 2015.

(51) Int. Cl.
*B01J 31/02* (2006.01)

(52) U.S. Cl.
CPC ...... *B01J 31/0255* (2013.01); *B01J 2231/321* (2013.01)

(58) Field of Classification Search
CPC .................. B01J 31/0255; B01J 2231/321
See application file for complete search history.

(56) References Cited

U.S. PATENT DOCUMENTS

| | | | |
|---|---|---|---|
| 4,608,239 A | 8/1986 | Devon | |
| 4,912,155 A | 3/1990 | Burton | |
| 5,840,647 A | 11/1998 | Puckette | |
| 6,130,358 A | 10/2000 | Tolleson | |
| 6,909,019 B1 | 6/2005 | Debenham | |
| 7,586,010 B2 | 9/2009 | Liu | |
| 7,674,937 B2 | 3/2010 | Tolleson | |
| 9,550,179 B1 * | 1/2017 | Puckette | ............ B01J 31/2295 |
| 2009/0171121 A1 | 7/2009 | Liu | |

OTHER PUBLICATIONS

Arshinova, R. P.; "Contemporary Ideas About the Conformations of Eight-membered Cyclic Systems with Planar Fragments"; Russian Chemical Reviews, 57 (12); 1988; pp. 1142-1161.
Klender, G. J. et al.; "Further Developments in the Study of Fluorophosphonite Stabilizers"; Polymer Preprints, 43 (2); 1993; pp. 156-157.
Klender, G. J. and Elnager, H. Y.; "The Preparation and Performance of "Cage" Diphosphites as Secondary Antioxidants in the Stabilization of Polyolefins"; Die Angewandte makromolekulare Chemie, 252; 1997; pp. 103-117.
Tolman, Chadwick A.; "Steric Effects of Phosphorus Ligands in Organometallic Chemistry and Homogeneous Catalysis"; Chemical Reviews, 77; 1977; p. 313.
Notification of Transmittal of the International Search Report and the Written Opinion of the International Searching Authority, or the Declaration dated Oct. 26, 2016 received in corresponding International Application No. PCT/US2016/047476.

* cited by examiner

*Primary Examiner* — Golam M M Shameem
(74) *Attorney, Agent, or Firm* — James Arnold, Jr.

(57) ABSTRACT

This invention pertains to hydroformylation catalysts containing a mixture of isomeric forms of halo-phosphorus ligands. This invention also describes a procedure for preparing isomers of certain halophosphite ligands, which contain the phosphorus atom in a macrocyclic ring.

20 Claims, 2 Drawing Sheets

HYDROFORMYLATION CATALYST

CROSS-REFERENCE TO RELATED APPLICATIONS

This application is a divisional of U.S. patent application Ser. No. 15/180,823, filed on Jun. 13, 2016; which claims priority to U.S. Provisional Application No. 62/216,038 filed Sep. 9, 2015; the disclosures of which are incorporated herein by reference in their entirety.

FIELD OF THE INVENTION

The invention generally relates to a mixture of halophosphite conformational isomers, methods of making the mixture, hydroformylation catalysts containing the mixture, and hydroformylation processes using the catalysts.

BACKGROUND OF THE INVENTION

The hydroformylation reaction, also known as the oxo reaction, is used extensively in commercial processes for preparing aldehydes by reacting one mole of an olefin with one mole each of hydrogen and carbon monoxide. The most extensive use of the reaction is in the preparation of normal- and isobutyraldehyde from propylene.

The ratio of the amount of the normal-aldehyde product to the amount of the iso-aldehyde product typically is referred to as the normal to iso (N:I or N/I) or the normal to branched (N:B or N/B) ratio.

In the case of propylene, the normal- and iso-butyraldehydes obtained from propylene are, in turn, converted into many commercially valuable chemical products, such as, for example, n-butanol, 2-ethyl-hexanol, n-butyric acid, iso-butanol, neo-pentyl glycol, 2,2,4-trimethyl-1,3-pentanediol, and the mono-isobutyrate and di-isobutyrate esters of 2,2,4-trimethyl-1,3-pentanediol. The hydroformylation of higher α-olefins (such as 1-octene, 1-hexene, and 1-tetradecene) yields aldehyde products that are useful feedstocks for preparing detergent alcohols and plasticizer alcohols.

U.S. Pat. Nos. 5,840,647 and 6,130,358 introduced a new concept in ligand design with the disclosure of halogen substituents on the phosphorus atom of trivalent phosphorus ligands. These halogenated phosphorus ligands are readily prepared, possess high activity and good stability, and permit a wide N/I range of products to be prepared by simply varying the process parameters.

Many of the halophosphite ligand compositions contain the phosphorus atom in a macrocyclic ring structure. Macrocyclic rings introduce the possibility of many different structural and conformational isomers of the phosphorus ligands. The presence of a plurality of isomeric forms of the phosphorus ligand can be problematic, because each of the different isomers can form complexes with the transition metal catalyst, and the reactivity and selectivity of the catalyst can vary greatly depending on which isomeric form of the phosphorus ligand is attached to the transition metal atom. Frequently, using mixed isomeric forms of the phosphorus ligand results in a complex catalyst composition, which makes it difficult to predict and control the activity and selectivity of the catalyst.

Thus, it is desirable to be capable of creating a catalyst composition from a mixture of phosphorus ligand isomers that behaves in a manner as if it were a single isomer of the phosphorus ligand. In addition or alternatively, it is desirable to have a process by which a single isomer can be isolated from a mixture of isomers.

The present invention addresses these desires as well as others, which will become apparent from the following description and the appended claims.

SUMMARY OF THE INVENTION

The invention is as set forth in the appended claims.

Briefly, in one aspect, the present invention provides a composition comprising conformational isomers A and B:

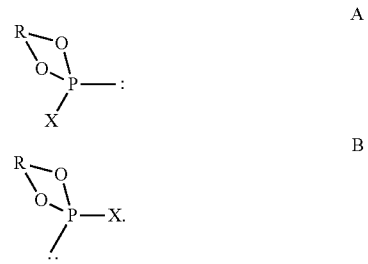

The lone pair of electrons on the phosphorus atom in isomer A is in a pseudo-equatorial orientation. The lone pair of electrons on the phosphorus atom in isomer B is in a pseudo-axial orientation. X is fluorine or chlorine. R is a divalent group having the formula 1:

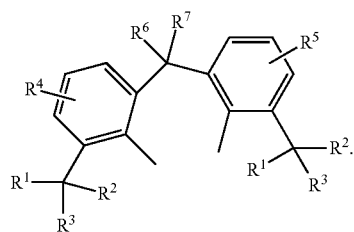

$R^1$, $R^2$, $R^3$, $R^4$, and $R^5$ are each independently hydrogen or a hydrocarbyl group containing 1 to 40 carbon atoms. $R^6$ and $R^7$ are each independently hydrogen or a hydrocarbyl group containing 1 to 10 carbon atoms with the proviso that at least one of $R^6$ and $R^7$ contains at least one carbon atom. The composition has a B:A molar ratio of greater than 1:1.

In another aspect, the present invention provides a method for separating conformational isomers. The method comprises:

(a) dissolving a feed mixture of the halophosphite conformational isomers A and B in a solvent to form a reactant solution;

(b) contacting the reactant solution with an alcohol in the presence of an acid catalyst at conditions effective to form a product mixture having a greater B:A molar ratio than the feed mixture; and (c) quenching the product mixture with water.

In yet another aspect, the present invention provides a catalyst composition comprising a transition metal (M) selected from Group VIIIB and rhenium, and a mixture of the halophosphite conformational isomers A and B. The molar ratio of B:A is such that the isomer B forms a complex with the transition metal. The molar ratio of A:M is 5 or less.

In yet another aspect, the present invention provides a catalyst solution, which comprises the catalyst composition according to the invention and a hydroformylation solvent.

In yet another aspect, the present invention provides a process for preparing an aldehyde. The process comprises contacting an olefin, hydrogen, and carbon monoxide with a catalyst solution according to the invention at conditions effective to form an aldehyde.

DETAILED DESCRIPTION OF THE INVENTION

Figure 1:
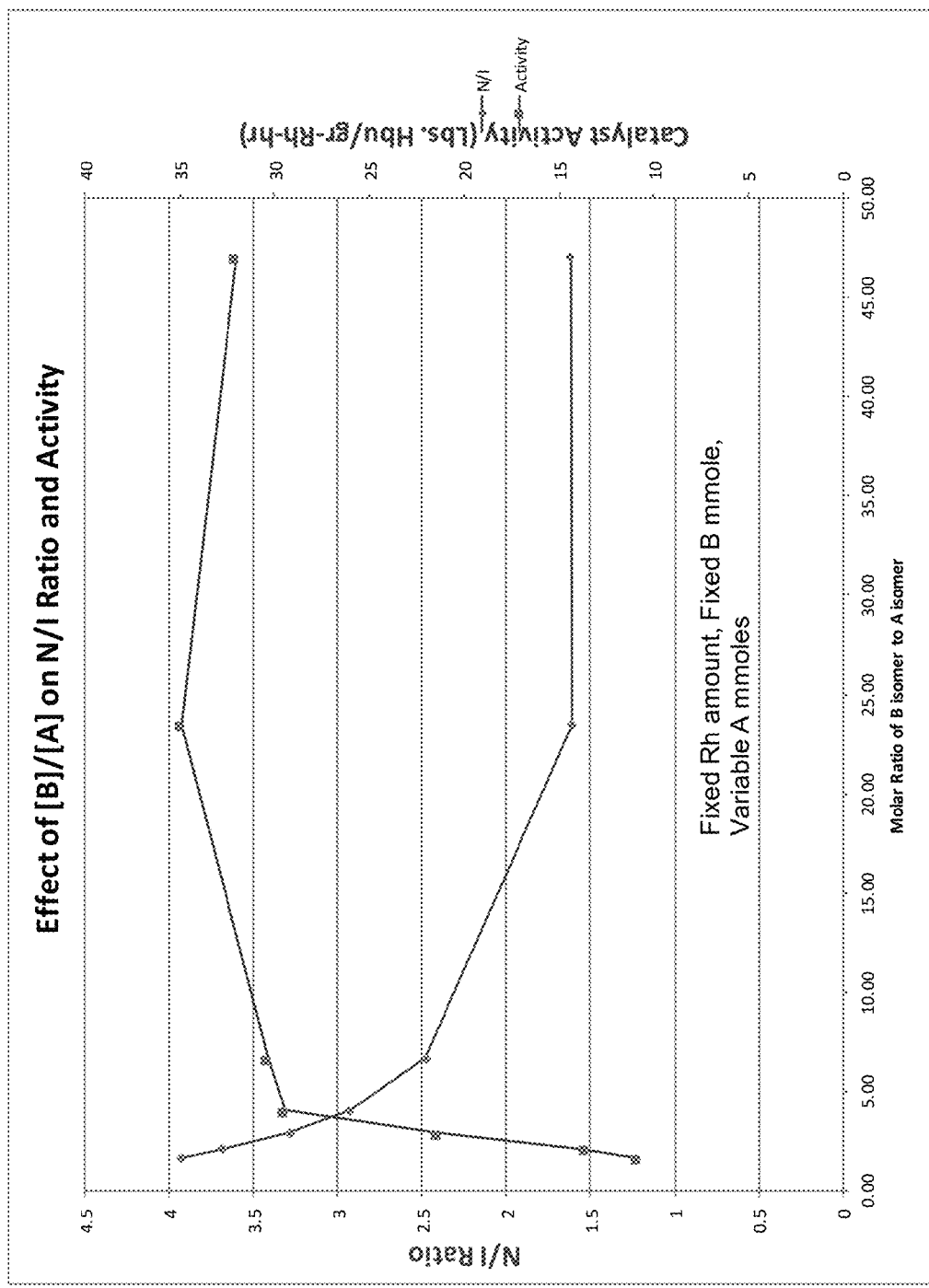
FIG. 1 is a graph of the effect of the molar ratio of B/A on the N/I product ratio and the catalyst activity based on the data from Example 4.

We have surprisingly discovered that the chemical reactivity of the "A" and "B" isomers of the cyclic fluorophosphite, Ethanox 398™, is indeed different, if the process conditions to which the material is subjected are less than the temperature needed to rapidly equilibrate the isomers. In the case of the Ethanox 398™ molecule, the "A" isomer will selectively bind to transition metals preferentially to the "B" isomer.

In this regard, solutions of rhodium dicarbonyl acetonylacetonate were prepared with mixtures of isomers, and when examined by NMR, the spectra indicated that the "A" isomer was preferentially bonded to the transition metal. Furthermore, in the specific case of Ethanox 398™ and rhodium, the "A" isomer formed a bis-ligated complex prior to the "B" isomer forming a mono-ligated complex.

We have also surprisingly discovered that if the differences between the reactivity of the "A" and "B" isomers are sufficiently great, then a mixture of the isomers will behave as if it were a single isomer. This selectivity in reactivity occurs if the ratio of the "A" and "B" isomers are maintained at a specific minimum ratio. Thus, it is possible to utilize a mixture of isomers to prepare a catalyst composition in which only one of the isomeric forms reacts to create transition metal complexes. As a result, the catalyst composition expresses the chemistry of only one of the isomeric forms of the phosphorus ligand. Such control of the chemistry allows for the use of mixed isomer samples to prepare a catalyst that behaves like it contains only a single isomer. The single isomer selectivity can be achieved without having to go through the difficulty of purifying out the pure isomers.

We have further surprisingly discovered that if the "B" isomer is used in a hydroformylation catalyst mixture that contains no "A" isomer or very small amounts of the "A" isomer, then the behavior of the catalyst is substantially changed when used in the hydroformylation reaction. Therefore, it is advantageous to carefully monitor the molar ratio of the "A" and "B" isomers in order to maintain the desired catalyst behavior. It is also advantageous to carefully monitor the "A" isomer and rhodium molar ratios as well as the ratio of "A" and "B" isomers. We have unexpectedly found that a "B" to "A" isomer ratio of 90:1 or greater can produce the effect of the "B" isomer alone. We have also unexpectedly found that if the "A" isomer to rhodium molar ratio is greater than 2.0, then the "A" isomer can dominate the chemistry of the catalyst. Blends of isomers with a "B" to "A" ratio of less than 90:1, but greater than 20:1, can still allow the "B" isomer to influence the chemistry of the catalyst; but a catalyst mixture with a "B" to "A" ratio of less than 20:1 tends to behave almost as if it were the "A" isomer alone provided that the "A" isomer to rhodium molar ratio is less than 2.0.

Thus, in one aspect, the present invention provides a composition comprising conformational isomers A and B:

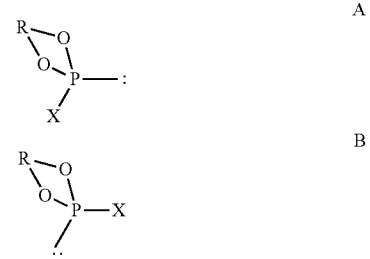

wherein
the lone pair of electrons on the phosphorus atom in isomer A is in a pseudo-equatorial orientation;
the lone pair of electrons on the phosphorus atom in isomer B is in a pseudo-axial orientation;
X is fluorine or chlorine;
R is a divalent group having the formula 1:

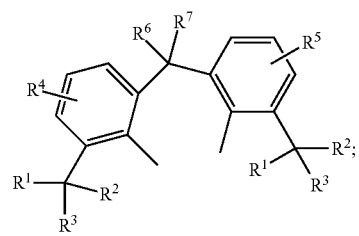

$R^1$, $R^2$, $R^3$, $R^4$, and $R^5$ are each independently hydrogen or a hydrocarbyl group containing 1 to 40 carbon atoms; and
$R^6$ and $R^7$ are each independently hydrogen or a hydrocarbyl group containing 1 to 10 carbon atoms with the proviso that at least one of $R^6$ and $R^7$ contains at least one carbon atom, and
wherein the composition has a B:A molar ratio of greater than 1:1.

The compounds contemplated in the present invention may be represented by the structure of formula 2:

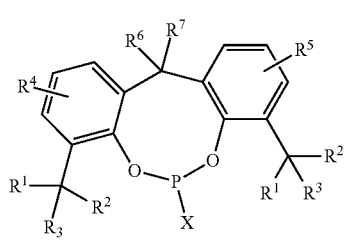

wherein $R^1$ to $R^7$ and X are as defined above.

In one embodiment, the molar ratio of B:A in the composition is 20 or greater. In another embodiment, the molar ratio of B:A in the composition is 30 or greater. In other embodiments, the molar ratio of B:A in the composition may be 40 or greater, 50 or greater, 60 or greater, 70 or greater, 80 or greater, 90 or greater, or 100 or greater. The upper limit of the molar ratio of B:A is not critical, and may be any practical value, for example, 1000 or less, 500 or less, 250 or less, 200 or less, or 150 or less.

In a preferred embodiment, R is a 2,2'-ethylidene bis(4,6-di-tert-butylphenyl) group.

In another preferred embodiment, X is fluorine.

When R is a 2,2'-ethylidene bis(4,6-di-tert-butylphenyl) group and X is fluorine, the compound is known as Ethanox 398™ in the trade. The structure of Ethanox 398™ and those of its A and B isomers are shown below.

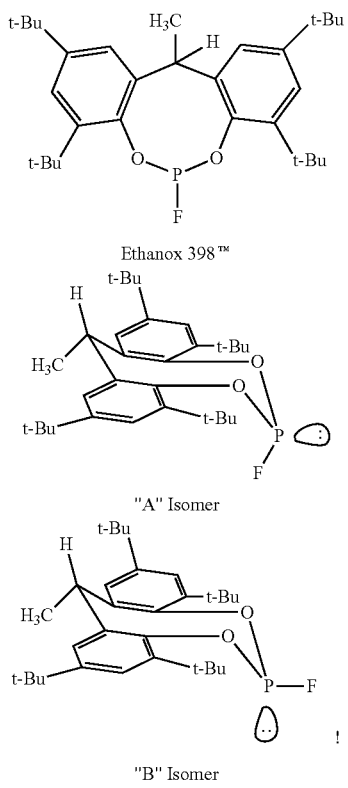

Ethanox 398™ and other compounds having the structure of formula 2 are generally commercially available. They may also be prepared according to the procedures described in U.S. Pat. No. 4,912,155. Such compounds are generally available in a B:A molar ratio of approximately 1:1 or less.

Compositions containing more B than A may be made according to a method of the invention. The method utilizes the differences in the reactivity of the two isomers in an acid catalyzed hydrolysis reaction.

Thus, in another aspect, the invention provides a method for separating conformational isomers. The method includes the steps of:
 (a) dissolving a feed mixture of the halophosphite conformational isomers A and B in a solvent to form a reactant solution;
 (b) contacting the reactant solution with an alcohol in the presence of an acid catalyst at conditions effective to form a product mixture having a greater B:A molar ratio than the feed mixture; and
 (c) quenching the product mixture with water.

In one embodiment, the method further comprises the steps of:

(d) cooling the product mixture to a sub-ambient temperature (e.g., 10° C. or less, 5° C. or less, 0° C. or less, −5° C. or less, or −10° C. or less) to precipitate the product; and
 (e) isolating the product by filtration.

The typical B:A molar ratio in the feed mixture can range from 1:1 to 0.7:1.

Steps (a)-(c) or (a)-(e) may be repeated until a product with the desired B:A molar ratio is obtained.

In one embodiment, the molar ratio of B:A in the product mixture is greater than 30:1. In other embodiments, the molar ratio of B:A in the product mixture is greater than 50:1, greater than 75:1, greater than 100:1, greater than 125:1, greater than 150:1, greater than 175:1, or greater than 200:1.

The solvent for dissolving the feed mixture is not particularly limiting. It may be any organic solvent capable of dissolving the isomers at ambient conditions or at elevated temperatures. Examples of such solvents include aromatic hydrocarbons, alcohols, and mixtures of both. The alcohols may be the same as those used to react with the isomer A. Examples of aromatic hydrocarbons include benzene, toluene, and xylene. Examples of alcohols include ethanol and 2-propanol. In one embodiment, the solvent comprises toluene. In another embodiment, the solvent comprises an ethanol or 2-propanol. In yet another embodiment, the solvent comprises both toluene and ethanol or 2-propanol.

The acid catalyst for use in the method of the invention is also not particularly limiting. It may be any acid capable of facilitating a hydrolysis reaction between the alcohol and the isomer A. Examples of suitable acid catalysts include sulfonic acids, such as p-toluenesulfonic acid, methanesulfonic acid, and benzenesulfonic acid.

In a typical method of the invention, the mixed isomers of the fluorophosphite are combined in a substantially dry toluene/alcohol mixture and then a strong acid, such as a sulfonic acid, is added to the reaction mixture. The mixture is heated for a specified period of time, quenched with water, cooled to sub-ambient temperatures to precipitate the product, and then the product is isolated by filtration.

The mixture of isomers A and B according to the invention is particularly useful as ligands for transition metals. The transition metal complexes are particularly useful as catalysts for hydroformylation reactions.

Thus, in yet another aspect, the present invention provides a catalyst composition comprising (a) a transition metal (M) selected from Group VIIIB and rhenium and (b) the mixture of halophosphite conformational isomers A and B. The molar ratio of B:A in the catalyst composition is such that the isomer B forms a complex with the transition metal. Moreover, the molar ratio of A:M is 5 or less.

As noted above, the molar ratio of B:A may be 20 or greater, 30 or greater, 40 or greater, or 90 or greater.

In one embodiment, the molar ratio of A:M is 4 or less. In another embodiment, the molar ratio of A:M is 3 or less. In yet another embodiment, the molar ratio of A:M is 2 or less.

Preferably, X in the isomers A and B in the catalyst composition is fluorine. Preferably, R in the isomers A and B in the catalyst composition is a 2,2'-ethylidene bis(4,6-di-tert-butylphenyl) group. In one embodiment, X in the isomers A and B in the catalyst composition is fluorine, and R is a 2,2'-ethylidene bis(4,6-di-tert-butylphenyl) group.

Preferably, the transition metal (M) in the catalyst comprises rhodium.

Rhodium compounds that may be used as a source of rhodium for the active catalyst include rhodium (II) or rhodium (III) salts of carboxylic acids, examples of which include di-rhodium tetraacetate dihydrate, rhodium(II) acetate, rhodium(II) isobutyrate, rhodium(II) 2-ethylhexanoate, rhodium(II) benzoate, and rhodium(II) octanoate. Also, rhodium carbonyl species such as $Rh_4(CO)_{12}$, $Rh_6(CO)_{16}$, and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the phosphite ligands of the present invention. Other rhodium sources include rhodium salts of strong mineral acids such as chlorides, bromides, nitrates, sulfates, phosphates, and the like.

Optionally, the catalyst composition according to the invention contains a hydroformylation solvent, although the reactant olefin and/or the product aldehyde may be used as the solvent.

The hydroformylation solvent may be selected from a wide variety of compounds, mixture of compounds, or materials that are liquid at the pressure at which the process is being operated. The main criterion for the solvent is that it dissolves the catalyst and the olefin substrate, and does not act as a poison to the catalyst. Such compounds and materials include various alkanes, cycloalkanes, alkenes, cycloalkenes, carbocyclic aromatic compounds, alcohols, esters, ketones, acetals, ethers and water. Specific examples of such solvents include alkane and cycloalkanes, such as dodecane, decalin, octane, iso-octane mixtures, cyclohexane, cyclooctane, cyclododecane, methylcyclohexane; aromatic hydrocarbons, such as benzene, toluene, xylene isomers, tetralin, cumene, alkyl-substituted aromatic compounds, such as the isomers of diisopropylbenzene, triisopropylbenzene and tert-butylbenzene; alkenes and cycloalkenes, such as 1,7-octadiene, dicyclopentadiene, 1,5-cyclooctadiene, octene-1, octene-2, 4-vinylcyclohexene, cyclohexene, 1,5,9-cyclododecatriene, 1-pentene; crude hydrocarbon mixtures, such as naphtha, mineral oils, and kerosene; high-boiling esters, such as 2,2,4-trimethyl-1,3-pentanediol diisobutyrate. The aldehyde product of the hydroformylation process also may be used. In practice, the preferred solvent is the higher boiling by-products that are naturally formed during the hydroformylation reaction and the subsequent steps, e.g., distillations, that are typically used for aldehyde product isolation.

Preferred solvents for the production of volatile aldehydes (e.g., propionaldehyde and the butyraldehydes) are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethyl-formamide, perfluorinated solvents (such as perfluoro-kerosene), sulfolane, water, and high-boiling hydrocarbon liquids as well as combinations of these solvents.

The concentration of the rhodium and ligand in the hydroformylation solvent or reaction mixture is not critical for the successful operation of the invention. A gram mole ligand:gram atom rhodium ratio of at least 1:1 normally is maintained in the reaction mixture. In order to obtain the desired selectivity of the catalyst, the molar ratio of the isomer with the axial lone pair of electrons and the isomer with the equatorial lone pair of electrons should be carefully monitored as well as the molar ratio of the isomer with the equatorial lone pair of electrons and rhodium.

As noted previously, it has been surprisingly found that an axial (B) to equatorial (A) isomer ratio of 90:1 or greater can yield the effect of the axial lone pair of electrons isomer (B) alone. It has also been surprisingly found that if the molar ratio of the isomer with the equatorial lone pair of electrons (A) to rhodium (M) is greater than 2.0, then the equatorial isomer (A) dominates the chemistry of the catalyst. Blends of isomers with an axial to equatorial (B:A) ratio of less than 90:1, but greater than 20:1, can still allow the axial isomer (B) to influence the chemistry of the catalyst, but a catalyst mixture with an axial to equatorial molar (B:A) ratio of less than 20:1 behaves almost as if it were the equatorial isomer alone.

The absolute concentration of rhodium in the reaction mixture or solution may vary from 1 mg/liter up to 5000 mg/liter or more. When the process is operated within the practical conditions of this invention, the concentration of rhodium in the reaction solution normally is in the range of about 20 to 300 mg/liter. Concentrations of rhodium lower than this range generally do not yield acceptable reaction rates with most olefin reactants and/or may require reactor operating temperatures that are so high as to be detrimental to catalyst stability. Higher rhodium concentrations are not preferred, because of the high cost of rhodium.

No special or unusual techniques are required for preparing the catalyst systems and solutions of the present invention, although it is preferred, to obtain a catalyst of high activity, that all manipulations of the rhodium and the phosphorus ligand components be carried out under an inert atmosphere, e.g., nitrogen, argon and the like. The desired quantities of a suitable rhodium compound and ligand are charged to the reactor in a suitable solvent. The sequence in which the various catalyst components or reactants are charged to the reactor is not critical.

The catalyst compositions and solutions of the invention are particularly suitable for preparing aldehydes.

Thus, in yet another aspect, the invention provides a process for preparing an aldehyde. The process comprises contacting an olefin, hydrogen, and carbon monoxide with the catalyst solution according to the invention at conditions effective to form an aldehyde.

The olefin used as the starting material is not particularly limiting and may be linear or cyclic olefins. Specifically, the olefin can be ethylene, propylene, butene, pentene, hexene, octene, styrene, non-conjugated dienes (such as 1,5-hexadiene), and blends of these olefins. Furthermore, the olefin may be substituted with functional groups so long as they do not interfere with the hydroformylation reaction. Suitable substituents on the olefin include any functional group that does not interfere with the hydroformylation reaction and includes groups such as carboxylic acids and derivatives thereof such as esters and amides, alcohols, nitriles, and ethers. Examples of substituted olefins include esters such as methyl acrylate or methyl oleate, alcohols such as allyl alcohol and 1-hydroxy-2,7-octadiene, and nitriles such as acrylonitrile.

The cyclic olefins that may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic, and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene, and 1,5,9-cyclododecatriene. The preferred olefin reactants include mono α-olefins of 2 to 10 carbon atoms, especially propylene. It has been found that cyclic olefins are sometimes less reactive than α-olefins, but that the lower reactivity can be overcome by adjusting process variables, such as the reaction temperature or the ligand to rhodium ratio.

Mixtures of olefins can also be used in the practice of this invention. The mixtures may be of the same carbon number, such as mixtures of n-octenes, or it may represent refinery distillation cuts, which typically contain a mixture of olefins over a range of several carbon numbers.

The reaction conditions used are not critical for the operation of the process, and conventional hydroformylation conditions normally can be used. The process involves contacting an olefin with hydrogen and carbon monoxide in the presence of the catalyst system described hereinabove. While the process may be carried out at temperatures in the range of about 20° to 200° C., the preferred hydroformylation reaction temperatures are from 50° to 135° C., with the most favored reaction temperatures ranging from 75° to 125° C. Higher reactor temperatures are not favored, because of increased rates of catalyst decomposition, while lower reactor temperatures can result in relatively slow reaction rates. The total reaction pressure may range from about ambient or atmospheric up to 70 bars absolute (about 1000 psig), preferably from about 8 to 28 bars absolute (about 100 to 400 psig).

The hydrogen:carbon monoxide mole ratio in the reactor likewise may vary considerably ranging from 10:1 to 1:10, and the sum of the absolute partial pressures of hydrogen and carbon monoxide may range from 0.3 to 36 bars absolute. The partial pressures of the ratio of the hydrogen to carbon monoxide in the feed is selected according to the linear:branched isomer ratio desired. Generally, the partial pressure of hydrogen and carbon monoxide in the reactor is maintained within the range of about 1.4 to 13.8 bars absolute (about 20 to 200 psia) for each gas. The partial pressure of carbon monoxide in the reactor is maintained within the range of about 1.4 to 13.8 bars absolute (about 20 to 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas—carbon monoxide and hydrogen) can be readily changed by the addition of either hydrogen or carbon monoxide to the syngas stream.

The amount of olefin present in the reaction mixture also is not critical. For example, relatively high-boiling olefins, such as 1-octene, may function both as the olefin reactant and the process solvent. In the hydroformylation of a gaseous olefin feedstock, such as propylene, the partial pressures in the vapor space in the reactor typically are in the range of about 0.07 to 35 bars absolute. In practice, the rate of reaction is favored by high concentrations of olefin in the reactor. In the hydroformylation of propylene, the partial pressure of propylene preferably is typically greater than 1.4 bars, e.g., from about 1.4 to 10 bars absolute. In the case of ethylene hydroformylation, the preferred partial pressure of ethylene in the reactor is greater than 0.14 bars absolute.

Any of the known hydroformylation reactor designs or configurations may be used in carrying out the process provided by the present invention. Thus, a gas-sparged, vapor take-off reactor design as disclosed in the examples set forth herein may be used. In this mode of operation, the catalyst, which is dissolved in a high boiling organic solvent under pressure, does not leave the reaction zone with the aldehyde product taken overhead by the unreacted gases. The overhead gases then are chilled in a vapor/liquid separator to condense the aldehyde product and the gases can be recycled to the reactor. The liquid product is let down to atmospheric pressure for separation and purification by conventional technique. The process may also be practiced in a batchwise manner by contacting the olefin, hydrogen, and carbon monoxide with the present catalyst in an autoclave.

A reactor design where catalyst and feedstock are pumped into a reactor and allowed to overflow with product aldehyde, i.e., liquid overflow reactor design, is also suitable. For example, high boiling aldehyde products, such as nonyl aldehydes, may be prepared in a continuous manner with the aldehyde product being removed from the reactor zone as a liquid in combination with the catalyst. The aldehyde product may be separated from the catalyst by conventional means, such as by distillation or extraction, and the catalyst then recycled back to the reactor. Water soluble aldehyde products can be separated from the catalyst by extraction techniques. A trickle-bed reactor design also is suitable for this process. It will be apparent to those skilled in the art that other reactor schemes may be used with this invention.

For continuously operating reactors, it may be desirable to add supplementary amounts of the phosphorus ligand over time to replace those materials lost by oxidation or other processes. This can be done by dissolving the ligand into a solvent and pumping it into the reactor as needed. The solvents that may be used include compounds that are found in the process, such as the reactant olefin, the product aldehyde, condensation products derived from the aldehyde, as well as other esters and alcohols that can be readily formed from the product aldehyde. Examples of such solvents include propionaldehyde, butyraldehyde, isobutyraldehyde, 2-ethylhexanal, 2-ethylhexanol, n-butanol, isobutanol, isobutyl isobutyrate, isobutyl acetate, butyl butyrate, propyl propionate, butyl propionate, butyl acetate, 2,2,4-trimethylpentane-1,3-diol diisobutyrate, and n-butyl 2-ethylhexanoate. Ketones, such as cyclohexanone, methyl isobutyl ketone, methyl ethyl ketone, diisopropylketone, and 2-octanone may also be used as well as trimeric aldehyde ester-alcohols, such as Texanol™ ester alcohol.

In one embodiment, the hydroformylation process according to the invention produces an aldehyde with an N/I molar ratio of 1 to 5. In another embodiment, the N/I molar ratio ranges from 1 to 4. In yet another embodiment, the N/I molar ratio ranges from 1 to 3 or from 1 to 2.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Example 1—Separation of Isomer B of Ethanox 398™

One kilogram of Ethanox 398™ with an A-to-B isomer molar ratio of 1.35:1 was dissolved into 1 liter of toluene and 2 liters isopropyl alcohol. The mixture was stirred and heated to 80° C. p-Toluenesulfonic acid (25 grams) was dissolved into 100 milliliters of isopropyl alcohol and then was slowly added to the hot toluene/isopropyl alcohol solution. The mixture was then stirred for one hour at 80° C. The progress of the reaction was monitored by gas chromatography and when the analysis showed a B/A molar ratio higher than 30, water (60 milliliters) was added to the hot solution. The reaction mixture was stirred overnight and allowed to cool to ambient temperature. The mixture was then chilled to −10° C. to finish the precipitation of the product. The solids were isolated by filtration, rinsed with 100 milliliters of isopropanol, and dried under $N_2$ for 24 hours to give the crude product. The crude product was normally 600-700 grams.

The crude product was typically combined into a double batch for the final purification. Two of the crude batches were combined with 1 liter of toluene and 2 liters isopropyl alcohol and heated to 80° C. p-Toluenesulfonic acid (10 grams) was dissolved into 100 milliliters of isopropyl alcohol and then was slowly added to the hot toluene/isopropyl alcohol solution. The mixture was then stirred for one hour at 80° C. The progress of the reaction was monitored by gas chromatography and when the analysis showed B/A molar ratio higher than 200, water (40 milliliters) was added to the hot solution. The reaction mixture was allowed to cool overnight and was then chilled to 0° C. to finish the precipitation of the product. The solids were isolated by filtration, rinsed with 100 milliliters of isopropanol, and dried under $N_2$ for 24 hours to give the final product. The typical yield for a double batch was 900 to 1100 grams of product with a B/A isomer molar ratio of >200 and a product purity of 90 wt % or higher.

Example 2—NMR Studies with "A" and "B" Isomers of Ethanox 398™

A solution of rhodium dicarbonyl acetonylacetonate containing 1.0 molar equivalent of rhodium and 2.0 molar equivalents of the "B" isomer of Ethanox 398™ was prepared in deutero chloroform. Phosphorus NMR showed the presence of mono-ligated rhodium species as a doublet of doublets with absorptions at 132, 134, 139 and 141 ppm as well as the free ligand as a doublet with absorptions at 129 and 137 ppm. Integration of the peaks showed that the ratio of the areas of the free ligand peaks to the complexed ligand peaks was 1.36. This is indicative that the ligand was forming predominantly a mono-ligated complex of rhodium, even with 2.0 equivalents of the "B" isomer.

Adding 1.0 equivalents of the "A" isomer to the mixture caused the peaks from the complexed "B" isomer to disappear and the appearance of a series of complex absorptions at 109 to 114 ppm and 117 to 121 ppm, which represent the "A" isomer complexed to the rhodium. The new absorptions appeared to be mixtures of mono-ligated and bis-ligated rhodium species. The uncomplexed "B" isomer was still present, but no uncomplexed or free "A" isomer was observed.

Adding a second molar equivalent of the "A" isomer caused the mono-ligated rhodium-"A" species to disappear and enhanced the signals from the bis-ligated rhodium-"A" species. A small amount of the non-complexed "A" ligand was also observed as a broad doublet with absorptions at 104 and 112 ppm.

These studies show that the "A" isomer will preferentially bind the rhodium atom and that the "A" isomer will rapidly displace the "B" isomer from rhodium complexes, even at very low concentrations.

Hydroformylation Process Set-Up

Propylene was reacted with hydrogen and carbon monoxide in a vapor take-off reactor made of a vertically arranged stainless steel pipe having a 2.5 cm inside diameter and a length of 1.2 meters to produce butyraldehydes. The reactor was encased in an external jacket that was connected to a hot oil machine. The reactor had a filter element located in the side near the bottom of the reactor for the inlet of gaseous reactants. The reactor contained a thermocouple, which was arranged axially with the reactor in its center for accurate measurement of the temperature of the hydroformylation reaction mixture. The bottom of the reactor had a high-pressure tubing connection that was connected to a cross. One of the connections to the cross permitted the addition of non-gaseous reactants (such as higher boiling alkenes or make-up solvents), another led to the high-pressure connection of a differential pressure (D/P) cell that was used to measure catalyst level in the reactor, and the bottom connection was used for draining the catalyst solution at the end of the run.

In the hydroformylation of propylene in a vapor take-off mode of operation, the hydroformylation reaction mixture or solution containing the catalyst was sparged under pressure with the incoming reactants of propylene, hydrogen, and carbon monoxide as well as any inert feed, such as nitrogen. As butyraldehyde was formed in the catalyst solution, it and unreacted reactant gases were removed as a vapor from the top of the reactor by a side-port. The removed vapor was chilled in a high-pressure separator where the butyraldehyde product was condensed along with some of the unreacted propylene. The uncondensed gases were let down to atmospheric pressure via the pressure control valve. These gases passed through a series of dry-ice traps where any other aldehyde product was collected. The product from the high-pressure separator was combined with that of the traps, and was subsequently weighed and analyzed by standard gas/liquid phase chromatography (GC/LC) techniques for the net weight and normal/iso ratio of the butyraldehyde product. Activity was calculated as kilograms of butyraldehydes produced per gram of rhodium per hour.

The gaseous feeds were introduced into the reactor via twin cylinder manifolds and high-pressure regulators. The hydrogen passed through a mass flow controller and then through a commercially available "Deoxo" (registered trademark of Engelhard Inc.) catalyst bed to remove any oxygen contamination. The carbon monoxide passed through an iron carbonyl removal bed (as disclosed in U.S. Pat. No. 4,608,239), a similar "Deoxo" bed heated to 125° C., and then a mass flow controller.

Nitrogen can be added to the feed mixture as an inert gas. Nitrogen, when added, was metered in and then mixed with the hydrogen feed prior to the hydrogen Deoxo bed. Propylene was fed to the reactor from feed tanks that were pressurized with hydrogen and was controlled using a liquid mass flow meter. All gases and propylene were passed through a preheater to ensure complete vaporization of the liquid propylene prior to entering the reactor.

Example 3—Hydroformylation of Propylene with Varying A and B Ratios—Effect of Isomer Ratios on Reaction Products A catalyst solution was prepared under nitrogen using a charge of 7.7 milligrams of rhodium (0.075 millimole, as rhodium 2-ethylhexanoate), various amounts of the ligands as indicated in Table 1, and 190 mL of dioctylphthalate. The mixture was stirred under nitrogen (and heated, if necessary) until a homogeneous solution was obtained.

The mixture was charged to the reactor in a manner described previously, and the reactor was sealed. The reactor pressure control was set at 17.9 bar (260 psig), and the external oil jacket on the reactor was heated to 95° C. Hydrogen, carbon monoxide, nitrogen, and propylene vapors were fed through the frit at the base of the reactor, and the reactor was allowed to build pressure. The hydrogen and carbon monoxide ($H_2$/CO ratio was set to be 1:1 or other desired ratio) were fed to the reactor at a rate of 6.8 liters/min, and the nitrogen feed was set at 1.0 liter/min. The propylene was metered as a liquid and fed at a rate of 1.89 liters/min (212 grams/hour). The temperature of the external oil was modified to maintain an internal reactor temperature of 95° C. The unit was usually operated for 3 to 5 hours, and hourly samples were taken. The hourly samples were analyzed as described above using a standard GC method. The last two to three samples of the run were used to determine the N/I ratio and catalyst activity.

The results of the bench unit runs are summarized in Table 1.

Runs 1 through 7 show the effect of increasing the amount of the "A" isomer in the catalyst mixture. The catalyst activity increased along with the N/I ratio as the presence of the "A" isomer increased. The data show that as the molar ratio of the "B" isomer to the "A" isomer fell below about 90:1, the "A" isomer began to influence the chemistry as reflected in the N/I ratio. As the molar ratio of the "B" isomer to the "A" isomer fell below about 20, the "A" isomer dominated the chemistry as the chemical results became indistinguishable from Run 9, which contained an excess of the "A" isomer.

Run 8 was made with a mixture of isomers in which the ratio of the "B" isomer to the "A" isomer was at 1.4. Based on the results of the previously discussed NMR studies and the isomer mixture of Run 8, it is expected that the rhodium atom would only form ligand complexes with the "A" isomer. The Runs 1 through 5 show the influence of increasing amounts of the "A" isomer and runs 6 through 8 show the results from a catalyst composition that is dominated by the "A" isomer.

Run 9 was made with a ligand mixture enriched in the "A" isomer at an "A" to "B" isomer ratio of 11:1. The chemistry and the properties of the catalyst in this run were dominated by the "A" isomer. This is reflected in the higher catalyst activity and normal-to-iso ratio.

Example 4—Hydroformylation of Propylene with Fixed Amounts of Rh and B, and Varying Amounts of A The procedure of Example 3 was repeated with the amounts of Rh, A, and B listed in Table 2 below. The results of each run are also reported in Table 2.

TABLE 2

| | Run No. | | | | | | |
|---|---|---|---|---|---|---|---|
| | 10 | 11 | 12 | 13 | 14 | 15 | 16 |
| Ligand B Amount (mmole) | 2.35 | 2.35 | 2.35 | 2.35 | 2.35 | 2.35 | 2.35 |
| Ligand A Amount (mmole) | 1.40 | 1.10 | 0.80 | 0.58 | 0.35 | 0.10 | 0.05 |
| Rh Amount (mg) | 5.00 | 5.00 | 5.00 | 5.00 | 5.00 | 5.00 | 5.00 |

TABLE 1

| Run No. | Ligand B Amount (mmole) | Molar Ratio of B to Rh | Ligand A Amount (mmole) | Molar Ratio of A to Rh | Molar Ratio of B to A | Catalyst Activity* | N/I Ratio |
|---|---|---|---|---|---|---|---|
| 1 | 3.375 | 45 | 0 | 0 | | 6.92 | 1.25 |
| 2 | 3.413 | 45.5 | 0.0375 | 0.5 | 91 | 9.16 | 1.38 |
| 3 | 3.450 | 46 | 0.075 | 1 | 46 | 11.1 | 1.53 |
| 4 | 3.488 | 46.5 | 0.113 | 1.5 | 31 | 12.3 | 1.54 |
| 5 | 3.525 | 47 | 0.150 | 2 | 23.5 | 13.9 | 1.56 |
| 6 | 3.563 | 47.5 | 0.188 | 2.5 | 19 | 14.2 | 1.64 |
| 7 | 3.750 | 50 | 0.375 | 5 | 10 | 14.9 | 1.81 |
| 8 | 0.515 | 6.8 | 0.375 | 5 | 1.4 | 10.5 | 1.71 |
| 9 | 0.034 | 0.45 | 0.375 | 5 | 0.091 | 13.4 | 1.69 |

*Catalyst activity is expressed as pounds of butyraldehyde formed per gram-Rh-hour (lbs. HBu/gr-Rh-hr).

TABLE 2-continued

| | Run No. | | | | | | |
|---|---|---|---|---|---|---|---|
| | 10 | 11 | 12 | 13 | 14 | 15 | 16 |
| Molar Ratio of Total Ligand/Rh | 77.18 | 71.00 | 64.83 | 60.30 | 55.57 | 50.42 | 49.39 |
| Molar Ratio of A/Rh | 28.81 | 22.64 | 16.46 | 11.94 | 76.20 | 2.06 | 1.03 |
| Molar Ratio of B/Rh | 48.36 | 48.36 | 48.36 | 48.36 | 48.36 | 48.36 | 48.36 |
| Molar Ratio of B/A | 1.68 | 2.14 | 2.94 | 4.05 | 6.71 | 23.50 | 47.00 |
| Product N/I Ratio | 3.93 | 3.69 | 3.29 | 2.93 | 2.48 | 1.61 | 1.62 |
| Catalyst Activity (lbs. HBu/gr-Rh-hour) | 10.88 | 13.66 | 21.42 | 29.46 | 30.34 | 34.9 | 32.02 |

FIG. 1 graphically shows the effect of the molar ratio of B/A on the N/I product ratio and the catalyst activity based on the data from Table 2.

Example 5—Hydroformylation of Propylene with Fixed Amounts of Rh and A, and Varying Amounts of B The procedure of Example 3 was repeated with the amounts of Rh, A, and B listed in Table 3 below. The results of each run are also reported in Table 3.

TABLE 3

| | Run No. | | | | | |
|---|---|---|---|---|---|---|
| | 17 | 18 | 19 | 20 | 21 | 22 |
| Ligand B Amount (mmole) | 0.37 | 0.36 | 0.20 | 1.00 | 2.00 | 0.70 |
| Ligand A Amount (mmole) | 0.76 | 0.77 | 0.76 | 0.76 | 0.76 | 0.76 |
| Rh Amount (mg) | 5.00 | 5.00 | 5.00 | 5.00 | 5.00 | 5.00 |
| Molar Ratio of Total Ligand/Rh | 23.26 | 23.26 | 19.76 | 36.22 | 56.80 | 30.05 |
| Molar Ratio of A/Rh | 15.64 | 15.85 | 15.64 | 15.64 | 15.64 | 15.64 |
| Molar Ratio of B/Rh | 7.61 | 7.41 | 4.12 | 20.58 | 41.16 | 14.41 |
| Molar Ratio of B/A | 0.49 | 0.47 | 0.26 | 1.32 | 2.63 | 0.92 |
| Product N/I Ratio | 3.53 | 3.73 | 3.16 | 3.34 | 3.21 | 3.33 |
| Catalyst Activity (lbs. HBu/gr-Rh-hr) | 17.77 | 14.68 | 21.5 | 19.12 | 27.21 | 22.84 |

Example 6—Hydroformylation of Propylene with Fixed Amounts of A and B, and Varying Amounts of Rh The procedure of Example 3 was repeated with the amounts of Rh, A, and B listed in Table 4 below. The results of each run are also reported in Table 4.

TABLE 4

| | Run No. | | | |
|---|---|---|---|---|
| | 23 | 24 | 25 | 26 |
| Ligand B Amount (mmole) | 4.1 | 4.1 | 4.1 | 4.1 |
| Ligand A Amount (mmole) | 0.21 | 0.21 | 0.21 | 0.21 |
| Rh Amount (mmole) | 0.0565 | 0.028 | 0.019 | 0.014 |
| Molar Ratio of Total Ligand/Rh | 76.28 | 153.93 | 226.84 | 307.86 |
| Molar Ratio of A/Rh | 3.72 | 7.50 | 11.05 | 15.00 |
| Molar Ratio of B/Rh | 72.57 | 146.43 | 215.79 | 292.86 |
| Molar Ratio of B/A | 19.52 | 19.52 | 19.52 | 19.52 |
| Product N/I Ratio | 1.9 | 2.11 | 2.12 | 2.5 |
| Catalyst Activity (lbs. HBu/gr-Rh-hour) | 37.43 | 19.34 | 14.44 | 7.57 |

Figure 2:
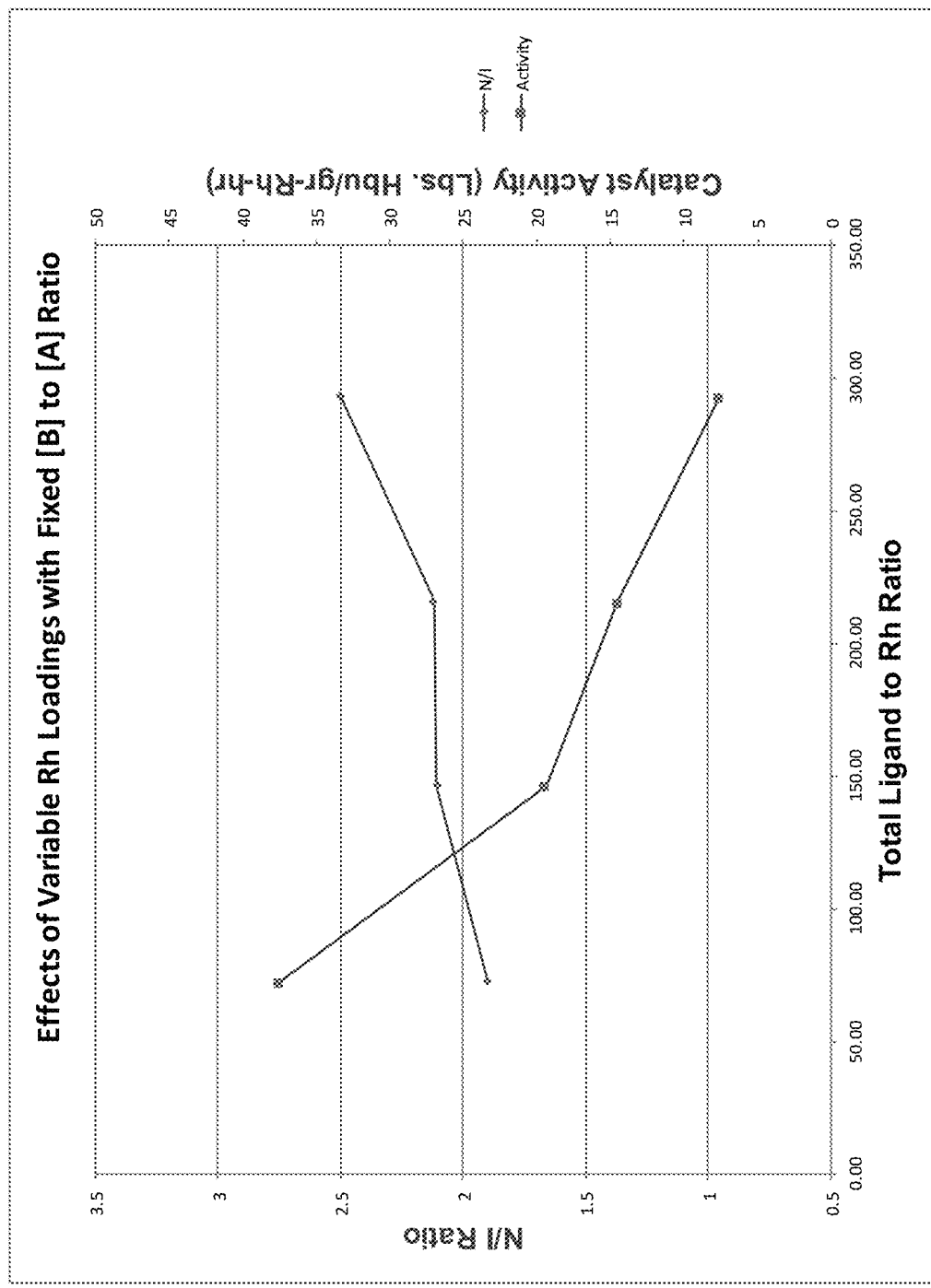
FIG. 2 is a graph of the effect of the Rh loading on the N/I product ratio and the catalyst activity based on the data from Example 6.

FIG. 2 graphically shows the effect of the Rh loading on the N/I product ratio and the catalyst activity based on the data from Table 4.

The invention has been described in detail with particular reference to preferred embodiments thereof, but it will be understood that variations and modifications can be effected within the spirit and scope of the invention.

We claim:

1. A catalyst composition comprising a transition metal (M) selected from Group VIIIB and rhenium, and a mixture of halophosphite conformational isomers A and B:

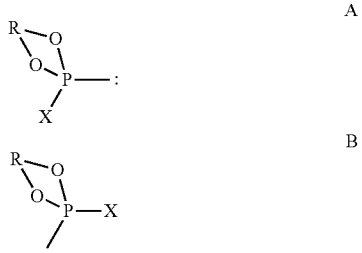

wherein
 the lone pair of electrons on the phosphorus atom in isomer A is in a pseudo-equatorial orientation;
 the lone pair of electrons on the phosphorus atom in isomer B is in a pseudo-axial orientation;
 X is fluorine or chlorine;
 R is a divalent group having the formula 1:

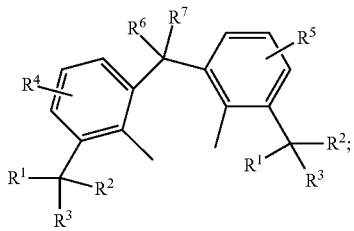

$R^1$, $R^2$, $R^3$, $R^4$, and $R^5$ are each independently hydrogen or a hydrocarbyl group containing 1 to 40 carbon atoms; and $R^6$ and $R^7$ are each independently hydrogen or a hydrocarbyl group containing 1 to 10 carbon atoms with the proviso that at least one of $R^6$ and $R^7$ contains at least one carbon atom, and wherein
(i) the molar ratio of B:A is such that the isomer B forms a complex with the transition metal, and
(ii) the molar ratio of A:M is 5 or less.

2. The catalyst composition comprising claim 1, wherein the molar ratio of B:A is 20 or greater.

3. The catalyst composition comprising claim 1, wherein the molar ratio of A:M is 4 or less.

4. The catalyst composition comprising claim 1 wherein X is fluorine.

5. The catalyst composition comprising claim 1, wherein R is a 2,2'-ethylidene bis(4,6-di-tert-butylphenyl) group.

6. The catalyst composition comprising claim 1, wherein the transition metal comprises rhodium.

7. A catalyst solution comprising:
a) a hydroformylation solvent, and
b) A catalyst composition comprising a transition metal (M) selected from Group VIIIB and rhenium, and a mixture of halophosphite conformational isomers A and B:

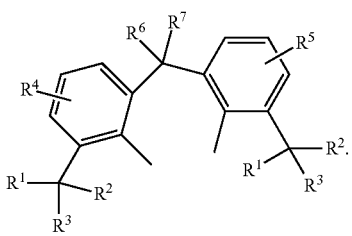

wherein
the lone pair of electrons on the phosphorus atom in isomer A is in a pseudo-equatorial orientation;
the lone pair of electrons on the phosphorus atom in isomer B is in a pseudo-axial orientation;
X is fluorine or chlorine;
R is a divalent group having the formula 1:

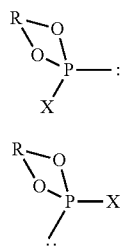

8. The catalyst solution comprising claim 7, wherein the hydroformylation solvent is selected from alkanes, cycloalkanes, alkenes, cycloalkenes, carbocyclic aromatic compounds, esters, ketones, acetals, ethers, and water.

9. A method for separating conformational isomers, the method comprising:
(a) dissolving a feed mixture of halophosphite conformational isomers A and B in a solvent to form a reactant solution:

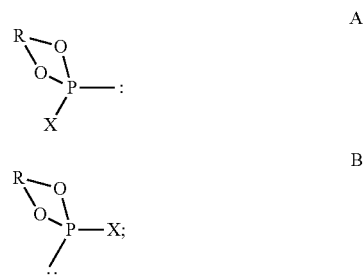

wherein
the lone pair of electrons on the phosphorus atom in isomer A is in a pseudo-equatorial orientation;
the lone pair of electrons on the phosphorus atom in isomer B is in a pseudo-axial orientation;
X is fluorine or chlorine;
R is a divalent group having the formula 1:

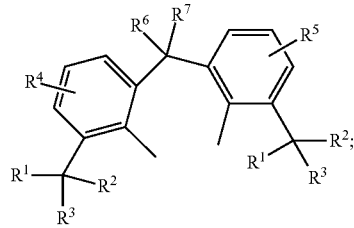

$R^1$, $R^2$, $R^3$, $R^4$, and $R^5$ are each independently hydrogen or a hydrocarbyl group containing 1 to 40 carbon atoms; and $R^6$ and $R^7$ are each independently hydrogen or a hydrocarbyl group containing 1 to 10 carbon atoms with the proviso that at least one of $R^6$ and $R^7$ contains at least one carbon atom;

(b) contacting the reactant solution with an alcohol in the presence of an acid catalyst at conditions effective to form a product mixture having a greater B:A molar ratio than the feed mixture; and (c) quenching the product mixture with water.

10. The method comprising claim 9, wherein the molar ratio of B:A in the feed mixture ranges from 1:1 to 0.7:1.

11. The method comprising claim 9, wherein the molar ratio of B:A in the product mixture is greater than 30:1.

12. The method comprising claim 9, wherein the molar ratio of B:A in the product mixture is greater than 200:1.

13. The method comprising claim 9, wherein the solvent comprises toluene.

14. The method comprising claim 13, wherein the solvent further comprises an alcohol.

15. The method comprising claim 14, wherein the alcohol comprises ethanol or 2-propanol.

16. The method comprising claim 9, wherein the acid catalyst comprises p-toluenesulfonic acid.

17. A composition comprising conformational isomers A and B:

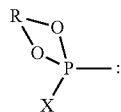
A

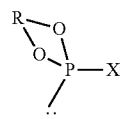
B wherein the lone pair of electrons on the phosphorus atom in isomer A is in a pseudo-equatorial orientation;

the lone pair of electrons on the phosphorus atom in isomer B is in a pseudo-axial orientation;

X is fluorine or chlorine;

R is a divalent group having the formula 1:

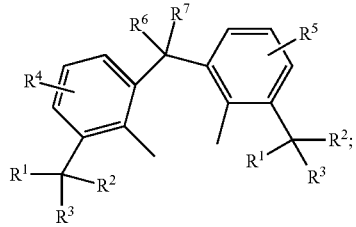
1

$R^1$, $R^2$, $R^3$, $R^4$, and $R^5$ are each independently hydrogen or a hydrocarbyl group containing 1 to 40 carbon atoms; and $R^6$ and $R^7$ are each independently hydrogen or a hydrocarbyl group containing 1 to 10 carbon atoms with the proviso that at least one of $R^6$ and $R^7$ contains at least one carbon atom, and wherein the composition has a B:A molar ratio of greater than 1:1.

18. The composition comprising claim 17, wherein the molar ratio of B:A is 20 or greater.

19. The composition comprising claim 17, wherein X is fluorine.

20. The composition comprising claim 17, wherein R is a 2,2'-ethylidene bis(4,6-di-tert-butylphenyl) group.

* * * * *